United States Patent
Haneda et al.

(10) Patent No.: US 12,365,860 B2
(45) Date of Patent: Jul. 22, 2025

(54) SCAFFOLDING MATERIAL FOR STEM CELL CULTURES AND STEM CELL CULTURE METHOD USING SAME

(71) Applicant: SEKISUI CHEMICAL CO., LTD., Osaka (JP)

(72) Inventors: Satoshi Haneda, Osaka (JP); Yuriko Manabe, Osaka (JP); Ryoma Ishii, Osaka (JP); Hiroki Iguchi, Osaka (JP); Yuhei Arai, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 188 days.

(21) Appl. No.: 16/958,218

(22) PCT Filed: Dec. 27, 2018

(86) PCT No.: PCT/JP2018/048391
§ 371 (c)(1),
(2) Date: Jun. 26, 2020

(87) PCT Pub. No.: WO2019/131982
PCT Pub. Date: Jul. 4, 2019

(65) Prior Publication Data
US 2021/0071147 A1 Mar. 11, 2021

(30) Foreign Application Priority Data

Dec. 27, 2017 (JP) ................. 2017-252420

(51) Int. Cl.
| | | |
|---|---|---|
| C12M 1/12 | (2006.01) | |
| C08F 124/00 | (2006.01) | |
| C08L 79/02 | (2006.01) | |
| C12M 3/00 | (2006.01) | |
| C12N 5/00 | (2006.01) | |
| C12N 5/0735 | (2010.01) | |
| C12N 5/074 | (2010.01) | |

(52) U.S. Cl.
CPC ........... C12M 25/14 (2013.01); C08F 124/00 (2013.01); C08L 79/02 (2013.01); C12M 21/06 (2013.01); C12N 5/0068 (2013.01); C12N 5/0606 (2013.01); C12N 5/0607 (2013.01); C12N 5/0696 (2013.01); C08L 2666/36 (2013.01); C12N 2533/30 (2013.01); C12N 2533/70 (2013.01)

(58) Field of Classification Search
CPC ...... C12M 25/14; C12M 21/06; C12M 23/20; C12M 25/02; C12M 25/06; C08F 124/00; C08F 8/28; C08L 79/02; C08L 2666/36; C12N 5/0068; C12N 5/0606; C12N 5/0607; C12N 5/0696; C12N 2533/30; C12N 2533/70; C12N 2501/727; C12N 5/0698

See application file for complete search history.

(56) References Cited

U.S. PATENT DOCUMENTS

| | | |
|---|---|---|
| 4,537,790 A | 8/1985 | Horodniceanu et al. |
| 5,393,668 A | 2/1995 | Cinatl et al. |
| 5,880,216 A | 3/1999 | Tanihara et al. |
| 6,984,692 B2 | 1/2006 | Kumaki et al. |
| 8,153,715 B2 | 4/2012 | Stark |
| 2002/0161440 A1 | 10/2002 | Son et al. |
| 2005/0164377 A1* | 7/2005 | Miyabayashi ....... C12N 5/0606 435/366 |
| 2006/0235084 A1 | 10/2006 | Heller et al. |
| 2007/0122901 A1 | 5/2007 | Morita et al. |
| 2009/0130756 A1 | 5/2009 | Klann et al. |
| 2009/0176937 A1 | 7/2009 | Frank et al. |
| 2011/0129924 A1 | 6/2011 | Ying et al. |
| 2011/0318829 A1* | 12/2011 | Tazaki .................. C12M 23/16 435/325 |
| 2012/0015177 A1 | 1/2012 | Kim |
| 2012/0202070 A1* | 8/2012 | Asanuma .......... B32B 17/10688 525/190 |
| 2013/0280725 A1 | 10/2013 | Ismagilov et al. |

(Continued)

FOREIGN PATENT DOCUMENTS

| | | |
|---|---|---|
| CN | 1216581 | 5/1999 |
| CN | 101528822 | 9/2009 |

(Continued)

OTHER PUBLICATIONS

Bayramoglu et al., "Preparation and Characterization of Poly(hydroxyethyl methacrylate-co-poly(ethyl-eneglycol-methacrylate)/Hydroxypropyl-chitosan) Hydrogel Films: Adhesion of Rat Mesenchymal Stem Cell," Macromolecular Research, 2011, vol. 19, No. 4, pp. 385-395.

Rebollar et al., "Physicochemical modifications accompanying UV laser induced surface structures on poly(ethyleneterephthalate) and their effect on adhesion of mesenchymal cell," Phys. Chem. Chem. Phys., 2014, vol. 16, pp. 17551-17559.

Togami et al., "Effects of water holding capability of the PVF sponge on the adhesion and differentiation of rat bone marrow stem cell culture," Society For Biomaterials, 2013, vol. 102A, No. 1, pp. 247-253.

(Continued)

*Primary Examiner* — Titilayo Moloye
(74) *Attorney, Agent, or Firm* — Wenderoth, Lind & Ponack, L.L.P.

(57) ABSTRACT

A scaffolding material for culturing a stem cell, which contains a synthetic resin, and has a storage elasticity at 100° C. of $1.0 \times 10^4$ Pa or more and $1.0 \times 10^8$ Pa or less, and a ratio between the storage elasticity at 25° C. and the storage elasticity at 100° C. ((storage elasticity at 25° C.)/(storage elasticity at 100° C.)) of $1.0 \times 10^1$ or more and $1.0 \times 10^5$ or less. The scaffolding material for stem cell culture has suitable hydrophilicity and strength, high fixation of stem cells after seeding, highly efficient cell proliferation, and excellent scratch resistance.

13 Claims, 4 Drawing Sheets

(56) References Cited

U.S. PATENT DOCUMENTS

| | | | |
|---|---|---|---|
| 2013/0309679 A1 | 11/2013 | Ismagilov et al. | |
| 2014/0210338 A1* | 7/2014 | Matsumura | C08K 5/56 252/301.36 |
| 2014/0315235 A1 | 10/2014 | Puschmann et al. | |
| 2015/0010919 A1 | 1/2015 | Feinberg et al. | |
| 2015/0140652 A1 | 5/2015 | Sasai et al. | |
| 2018/0126713 A1* | 5/2018 | Glaser | B32B 27/36 |
| 2018/0194935 A1 | 7/2018 | Maeda et al. | |
| 2019/0106561 A1* | 4/2019 | Ukidwe | B32B 27/308 |
| 2020/0362289 A1 | 11/2020 | Haneda et al. | |
| 2020/0399576 A1 | 12/2020 | Haneda et al. | |
| 2020/0407672 A1 | 12/2020 | Haneda et al. | |
| 2021/0071147 A1 | 3/2021 | Haneda et al. | |
| 2022/0227898 A1 | 7/2022 | Iguchi et al. | |

FOREIGN PATENT DOCUMENTS

| | | | |
|---|---|---|---|
| CN | 104428651 | 3/2015 | |
| CN | 107406652 A * | 11/2017 | C08F 8/28 |
| EP | 0339371 | 11/1989 | |
| EP | 0 897 000 | 2/1999 | |
| EP | 2 385 105 | 11/2011 | |
| EP | 2 821 789 | 1/2015 | |
| EP | 3 733 834 | 11/2020 | |
| EP | 4 286 508 | 12/2023 | |
| JP | H06153905 A * | 6/1994 | |
| JP | 9-131397 | 5/1997 | |
| JP | 10-52268 | 2/1998 | |
| JP | 10-204204 | 8/1998 | |
| JP | 2001-89574 | 4/2001 | |
| JP | 2001/131325 | 5/2001 | |
| JP | 2006-42758 | 2/2006 | |
| JP | 2006-272002 | 10/2006 | |
| JP | 2006-314285 | 11/2006 | |
| JP | 2009-39138 | 2/2009 | |
| JP | 2009-273444 | 11/2009 | |
| JP | 2010091689 A * | 4/2010 | |
| JP | 2010-158180 | 7/2010 | |
| JP | 2010-168444 | 8/2010 | |
| JP | 4956753 B2 * | 6/2012 | C12M 23/20 |
| JP | 2015-142525 | 8/2015 | |
| JP | 2015-195752 | 11/2015 | |
| JP | 2015-205462 | 11/2015 | |
| JP | 2015199932 A * | 11/2015 | |
| JP | 2016186044 A * | 10/2016 | |
| JP | 2017-23008 | 2/2017 | |
| JP | 2017-46676 | 3/2017 | |
| JP | 6144437 | 6/2017 | |
| JP | 2017-163898 | 9/2017 | |
| JP | 6427450 B2 * | 11/2018 | |
| KR | 2007-0122519 | 12/2007 | |
| TW | 201540829 | 11/2015 | |
| WO | 97/41216 | 11/1997 | |
| WO | 01/05877 | 1/2001 | |
| WO | WO2006093207 A1 * | 8/2008 | |
| WO | WO-2012023518 A1 * | 2/2012 | C09D 129/14 |
| WO | 2013/183777 | 12/2013 | |
| WO | 2015/129837 | 9/2015 | |
| WO | 2016/122123 | 8/2016 | |
| WO | 2017/057663 | 4/2017 | |

OTHER PUBLICATIONS

Saha et al., "Surface-engineered substrates for improved human pluripotent stem cell culture under fully defined conditions," PNAS, 2011, vol. 108, No. 46, pp. 18714-18719.

Tunma et al., "Improving the attachment and proliferation of umbilical cord mesenchymal stem cells on modified polystyrene by nitrogen-containing plasma," Cytotechnology, 2013, vol. 65, pp. 119-134.

Togami et al., "Effects of the water-holding capability of polyvinyl formal sponges on osteogenic ability in in vivo experiments," Society For Biomaterials, 2014, vol. 103B Issue 1, pp. 188-194.

Miyoshi et al., "Three-dimensional culture of mouse bone marrow cells within a porous polymer scaffold: effects of oxygen concentration and stromal layer on expansion of haematopoietic progenitor cells," Journal of Tissue Engineering and Regenerative Medicine, 2011, vol. 5, pp. 112-118.

Notice of Ground of Rejection mailed on Apr. 14, 2020 in Japanese Patent Application No. 2019-562491 with English-language translation.

Translation of The International Preliminary Report on Patentability issued Jul. 9, 2020 in International (PCT) Application No. PCT/JP2018/048389.

Translation of The International Preliminary Report on Patentability issued Jul. 9, 2020 in International (PCT) Application No. PCT/JP2018/048391.

Translation of The International Preliminary Report on Patentability issued Jul. 2, 2020 in International (PCT) Application No. PCT/JP2018/048386.

Extended European Search Report issued Oct. 12, 2021 in corresponding European Patent Application No. 18893580.3, 8 pages.

Extended European Search Report issued Dec. 23, 2021 in corresponding European Patent Application No. 18893713.0, 7 pages.

First Examination Report issued Jun. 14, 2022 in corresponding Indian Patent Application No. 202047029411, 7 pages.

Office Action issued Feb. 10, 2023 in U.S. Appl. No. 16/919,452, 23 pages.

Extended European Search Report issued Oct. 8, 2021 in corresponding European Patent Application No. 18897018.0, 8 pages.

Office Action issued Jan. 20, 2023 in U.S. Appl. No. 16/958,204, 22 pages.

Office Action issued Jan. 26, 2023 in U.S. Appl. No. 16/958,182, 28 pages.

Poly(vinylamine), Polymer source, Inc., downloaded on Jan. 19, 2023 from www.polymersource.ca/index.php?route=product, one page (Year: 2023).

Office Action issued Jun. 22, 2023 in U.S. Appl. No. 16/919,452, 13 pages.

Official Communication dated Sep. 18, 2023 issued in corresponding Indian Patent Application No. 202047029416, 2 pages.

Office Action issued Jun. 27, 2023 in U.S. Appl. No. 16/958,182, 18 pages.

Lee et al., "Cell Behavior on Polymer Surfaces With Different Functional Groups", Science and Technology of Polymers and Advanced Materials, Edited by P.N. Prasad et al., Plenum Press, New York, p. 535-545 (Year: 1998), 11 pages.

Office Action issued Jul. 12, 2023 in U.S. Appl. No. 16/919,312, 28 pages.

Office Action issued Aug. 14, 2023 in corresponding U.S. Appl. No. 16/958,204.

Office Action issued Nov. 21, 2023 in corresponding U.S. Appl. No. 16/919,452, 12 pages.

Office Action dated Mar. 4, 2024 in relevant U.S. Appl. No. 16/919,312.

Extended European Search Report issued Jan. 31, 2024 in corresponding European Patent Application No. 23203425.6.

Examination report No. 1 issued Nov. 1, 2023 in Australian Patent Application No. 2018398052.

Examination report issued Nov. 16, 2023 in corresponding Australian Patent Application No. 2018398050, 3 pages.

Chen Huipeng (ed.), "Advances in Pharmaceutical Bioengineering", People's Military Medical Press, Jul. 2004, p. 259, with English-language translation.

Wang Yingjun (ed), "Biomedical Ceramic Materials", South China University of Technology Press, Oct. 2010, pp. 167-168, with English-language translation.

Wang Mengzhong, et al."Handbook of Adhesion Application", Chemical Industry Press, Dec. 12, 2023, pp. 1-6.

Office Action issued Jun. 17, 2024 in related U.S. Appl. No. 16/958,204.

* cited by examiner

[FIG. 2]
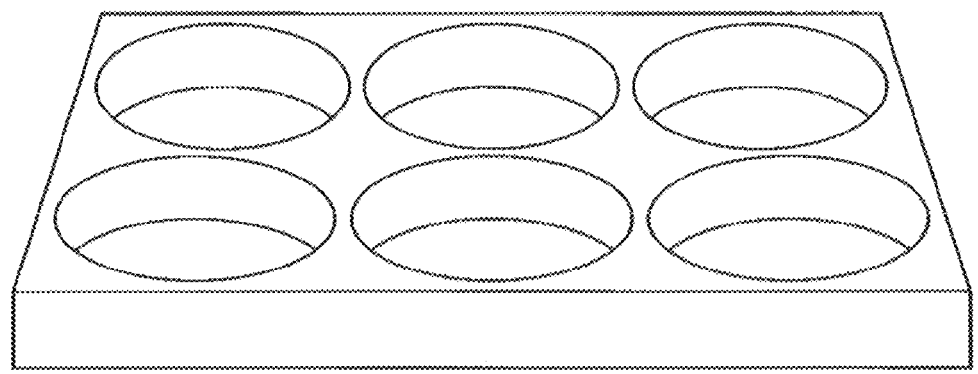

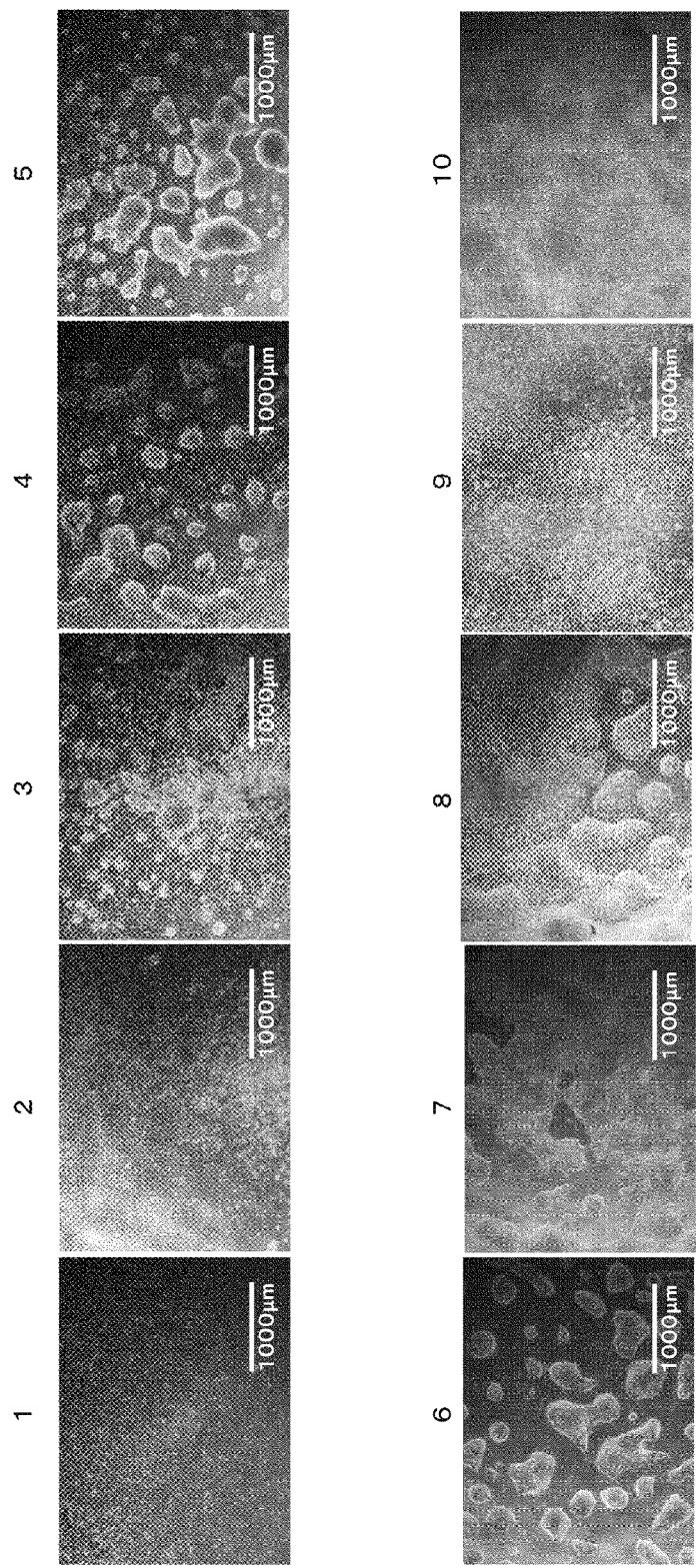
[FIG. 3]

SCAFFOLDING MATERIAL FOR STEM CELL CULTURES AND STEM CELL CULTURE METHOD USING SAME

TECHNICAL FIELD

The present invention relates to a scaffolding material for stem cell culture and a stem cell culture method using the same.

BACKGROUND ART

Stem cells are expected to be applied to drug discovery and regenerative medicine. Stem cells are cells that have self-renew potency and differentiation potency, including pluripotent stem cells that can differentiate into all cell types, and tissue stem cells and tissue progenitor cells that can differentiate only into constituent cell types of the body tissue in the same series. Examples of the pluripotent stem cells include human pluripotent stem cells (hPSCs) such as human embryonic stem cells (hESCs) and human induced pluripotent stem cells (hiPSCs). It is an essential basic technology to cultivate and proliferate stem cells safely and with good reproducibility for medical application of these cells. In particular, for industrial application on regenerative medicine, it is necessary to handle a large amount of stem cells in an undifferentiated state. Accordingly, extensive studies have been conducted on techniques for proliferating stem cells using natural and synthetic macromolecules and feeder cells, and maintaining the pluripotency (or multipotency). In particular, it is known that cell fixation after seeding is extremely high when an adhesive protein such as laminin or vitronectin, or a matrigel derived from mouse sarcoma is used as a natural polymer.

However, there are problems in that natural polymers are expensive because of their very low productivity, variations between lots can be seen because they are naturally occurring substances, and there are safety concerns due to animal-derived components.

In order to solve the above problems, a stem cell culture resin carrier using a synthetic resin has been proposed. For example, the column of Examples in Patent Document 1 discloses a polyvinyl acetal compound having a degree of acetalization of 20 to 60 mol % in order to provide a scaffold having excellent hydrophilicity and water resistance in culturing mouse fibroblasts. The column of Examples in Patent Document 2 discloses a hydrogel composed of an acrylic polymer in culturing mouse ES cells. The column of Examples in Patent Document 3 discloses a hydrophilic and flexible polyrotaxane gel in culturing mouse iPS cells.

RELATED ART DOCUMENT

Patent Document

Patent Document 1: JP 2006-314285 A
Patent Document 2: JP 2010-158180 A
Patent Document 3: JP 2017-23008 A

SUMMARY OF THE INVENTION

Problems to be Solved by the Invention

However, Patent Document 1 has a problem in that the scaffolding material resin is swelled in a medium due to its high hydrophilicity, and thus is peeled off. In addition, there is a problem in that the fixation of stem cells or pluripotent stem cells after seeding is so low that the cells do not proliferate sufficiently. In Patent Document 2, sodium 2-acrylamido-2-methylpropane sulfonate, sodium p-styrene sulfonate and N,N'-dimethylacrylamide are used, so that there is a problem in that the scaffolding material resin is swelled in a medium due to its high hydrophilicity, and thus is peeled off. Patent Document 3 has a problem in that the scaffolding material resin is swelled in a medium due to its high hydrophilicity, and thus is peeled off. There is a problem in that the scaffolding material is so flexible that differentiation into cardiomyocytes is promoted.

Furthermore, there is a problem in that in the seeding step of seeding stem cells in a culture container, the coating film is peeled off when the pipette tip hits the bottom of the culture container, causing variation between test lots.

As described above, there have been needs of a scaffolding material for stem cell culture having suitable hydrophilicity and strength, and a stem cell culture method using the same.

An object of the present invention is to provide a scaffolding material for stem cell culture having suitable hydrophilicity and strength, high fixation of stem cells after seeding, highly efficient cell proliferation, and excellent scratch resistance, and a stem cell culture method using the same.

Means for Solving the Problems

The present invention relates to the followings.
(1) A scaffolding material for culturing a stem cell, the scaffolding material comprising a synthetic resin, and having
a storage elasticity at 100° C. of $1.0 \times 10^4$ Pa or more and $1.0 \times 10^8$ Pa or less, and a ratio between the storage elasticity at 25° C. and the storage elasticity at 100° C. ((storage elasticity at 25° C.)/(storage elasticity at 100° C.)) of $1.0 \times 10^1$ or more and $1.0 \times 10^5$ or less.
(2) The scaffolding material for culturing a stem cell according to (1), in which the synthetic resin is a polyvinyl acetal resin.
(3) The scaffolding material for culturing a stem cell according to (1) or (2), in which the stem cell is a pluripotent stem cell.
(4) A container for culturing a stem cell, including the scaffolding material for culturing a stem cell according to any one of (1) to (3).

Effect of the Invention

According to the present invention, there are provided a scaffolding material for stem cell culture having suitable hydrophilicity and strength, and high fixation of stem cells after seeding, and a stem cell culture method using the same.

BRIEF DESCRIPTION OF DRAWINGS

FIG. 2 is a schematic perspective view of the 6-well type container for stem cell culture according to an embodiment.
FIG. 3 is a view showing evaluation criteria for cell proliferation 5 days after cell seeding.

MODES FOR CARRYING OUT THE INVENTION

Figure 1A:
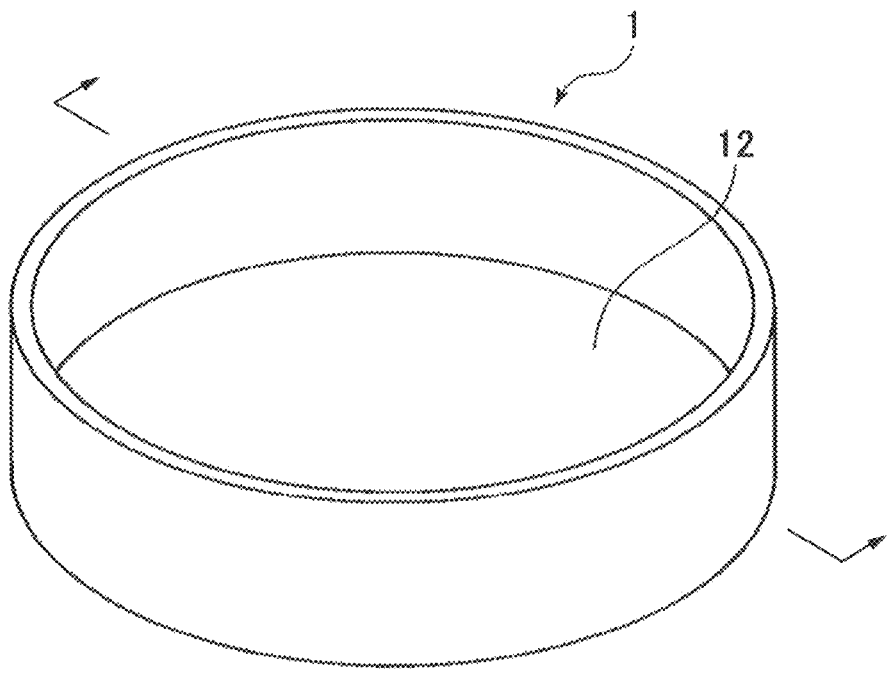
FIG. 1A is a schematic perspective view of the container for stem cell culture according to an embodiment.

Hereinafter, a description is made of the present invention with reference to embodiments, but the present invention is not limited to the following embodiments.

[Scaffolding Material for Stem Cell Culture]

In order to solve the above problems, as a result of intensive studies from the viewpoint of the physical properties of a synthetic resin, the present inventors have found that the above problems can be solved by using a synthetic resin having a predetermined storage elasticity, and thus have completed the present invention. In other words, the present invention relates to a scaffolding material for stem cell culture containing a synthetic resin, wherein the storage elasticity at 100° C. is $1.0 \times 10^4$ Pa or more and $1.0 \times 10^8$ Pa or less, and the ratio between the storage elasticity at 25° C. and the storage elasticity at 100° C. ((storage elasticity at 25° C.)/(storage elasticity at 100° C.)) is $1.0 \times 10^1$ or more and $1.0 \times 10^5$ or less.

The scaffolding material for stem cell culture has so suitable hydrophilicity and strength that the fixation of stem cells after seeding is improved. In particular, in a serum-free medium culture containing no feeder cell or adhesive protein, the initial fixation rate of stem cells after seeding is improved.

From the viewpoint of more suitable adhesion of stem cells, the storage elasticity at 100° C. of the resin film is more preferably $1.0 \times 10^5$ Pa or more and $1.0 \times 10^7$ Pa or less, still more preferably $2.0 \times 10^5$ Pa or more and $8.0 \times 10^6$ Pa or less, even more preferably $3.0 \times 10^5$ Pa or more and $5.0 \times 10^6$ Pa or less.

From the viewpoint of more suitable adhesion of stem cells, the storage elasticity at 25° C. of the resin film is preferably $1.0 \times 10^8$ Pa or more and $1.0 \times 10^{10}$ Pa or less, more preferably $3.0 \times 10^8$ Pa or more and $8.0 \times 10^9$ Pa, still more preferably $5.0 \times 10^8$ Pa or more and $5.0 \times 10^9$ Pa.

The ratio between the storage elasticity at 25° C. and the storage elasticity at 100° C. of the resin film is preferably $1.0 \times 10^1$ or more and $1.0 \times 10^5$ or less, more preferably $1.0 \times 10^2$ or more and $1.0 \times 10^4$ or less. When the value of the storage elasticity at 25° C. and the value of the storage elasticity at 100° C., and the ratio between the storage elasticity at 25° C. and the storage elasticity at 100° C. are in the above ranges, the bottom of the culture container is not scratched with the pipette tip, and stem cells can be suitably adhered because the elasticity changes under the culturing condition at 37° C. in the seeding step.

From the viewpoint of suitable adhesion of stem cells, the glass transition point of the resin film is preferably −30° C. or more and 95° C. or less, more preferably 0° C. or more and 90° C. or less, still more preferably 20° C. or more and 90° C. or less.

The storage elasticity and the glass transition point can be measured by the following method. Specifically:
1. A sheet is formed having a thickness of 500 μm by stacking samples by hot pressing.
2. The obtained sheet is measured under tensile conditions (frequency of 10 Hz, and temperature rising rate of 5° C./min in a temperature range from −150° C. to 150° C.) caused by dynamic viscoelasticity measuring device (DVA-200, manufactured by IT Keep Measurement Control Co., Ltd.). The storage elasticity at 25° C./storage elasticity at 100° C. is calculated by determining a storage elasticity at 25° C. and a storage elasticity at 100° C. from the obtained graph of the tensile storage elasticity.
3. The peak temperature of the loss sine is determined from the graph obtained by measurement of the storage elasticity, and is defined as a glass transition temperature Tg.

As to the storage elasticities at 100° C. and 25° C., the storage elasticity can be improved by, for example, introducing a rigid functional group or a functional group having high crystallinity into the main chain and the side chain to reduce the mobility of the polymer chain.

On the other hand, the storage elasticity can be lowered by introducing a flexible functional group or a functional group having low crystallinity into the main chain and the side chain to reduce the mobility of the polymer chain.

The scaffolding material for stem cell culture is not particularly limited for component as long as the above-mentioned requirements are satisfied, but preferably contains a synthetic resin.

The synthetic resin refers to a resin mainly composed of a polymer (hereinafter, also simply referred to as "polymer") obtained by polymerizing (including polycondensing) a polymerizable monomer (hereinafter, also simply referred to as "monomer"). The polymer also includes a copolymer of one or two or more polymerizable monomers.

Examples of the polymer include a polymer composed of one or more polymerizable monomers selected from the group consisting of (un)saturated hydrocarbons, aromatic hydrocarbons, (un)saturated fatty acids, aromatic carboxylic acids, (un)saturated ketones, aromatic ketones, (un)saturated alcohols, aromatic alcohols, (un)saturated amines, aromatic amines, (un)saturated thiols, aromatic thiols and organosilicon compounds.

Specific examples of the polymer include polyolefin, polyether, polyvinyl alcohol, polyvinyl acetal, polyester, poly(meth)acrylic ester, epoxy resin, polyamide, polyimide, polyurethane, polycarbonate, cellulose and polypeptide. Among them, from the viewpoint of stem cell fixation, poly(meth)acrylic ester and polyvinyl acetal are preferable, and polyvinyl acetal is more preferable.

These polymers may be used alone or in combination of two or more. When two or more polymers are combined, they may be used as a mixture, or may be used as a polymer in which the skeletons of the two or more polymers are chemically bonded. In addition, the structure of copolymer may be of a graft copolymer or a block copolymer, or a combination thereof. Accordingly, when a plurality of them are combined as a synthetic resin, it is preferable to combine poly(meth)acrylic ester and polyvinyl acetal.

In the present specification, the poly(meth)acrylic ester is not only polymers obtained by polymerizing a monomer, (meth)acrylic ester, but also includes those obtained by copolymerizing a monomer in addition to (meth)acrylic ester.

The (meth)acrylic ester is not particularly limited, but preferably contains at least one selected from the group consisting of alkyl (meth)acrylic esters, cyclic alkyl (meth)acrylic esters, aryl (meth)acrylic esters, (meth)acrylamides, polyethylene glycol (meth)acrylates and phosphorylcholine (meth)acrylates.

Examples of the alkyl (meth)acrylic ester include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth)acrylate, nonyl (meth)acrylate, isononyl (meth)acrylate, decyl (meth)acrylate, isodecyl (meth)acrylate, lauryl (meth)acrylate, stearyl (meth)acrylate and isotetradecyl (meth)acrylate.

These alkyl (meth)acrylic esters are not particularly limited, but the hydrogen atom may be substituted with various substituents including an alkoxy group having 1 to 3 carbon atoms and a tetrahydrofurfuryl group. Examples of the alkyl (meth)acrylic ester in which the hydrogen atom is substituted by the substituent include methoxyethyl acrylate and tetrahydrofurfuryl acrylate.

Examples of the cyclic alkyl (meth)acrylic ester include cyclohexyl (meth)acrylate and isobornyl (meth)acrylate.

Examples of the aryl (meth)acrylic ester include phenyl (meth)acrylate and benzyl (meth)acrylate.

Examples of the acrylamide include (meth)acrylamide, N-isopropyl (meth)acrylamide, N-tert-butyl (meth)acrylamide, N,N'-dimethyl (meth)acrylamide, (3-(meth)acrylamidopropyl) trimethylammonium chloride, 4-(meth)acryloylmorpholine, 3-(meth)acryloyl-2-oxazolidinone, N-[3-(dimethylamino) propyl] (meth)acrylamide, N-(2-hydroxyethyl) (meth)acrylamide, N-methylol (meth)acrylamide and 6-(meth)acrylamidohexanoic acid.

Examples of the polyethylene glycol (meth)acrylate include methoxy-polyethylene glycol (meth)acrylate, ethoxy-polyethylene glycol (meth)acrylate, hydroxy-polyethylene glycol (meth)acrylate, methoxy-diethylene glycol (meth)acrylate, ethoxy-diethylene glycol (meth)acrylate, hydroxy-diethylene glycol (meth)acrylate, methoxy-triethylene glycol (meth)acrylate, ethoxy-triethylene glycol (meth)acrylate and hydroxy-triethylene glycol (meth)acrylate.

Examples of the phosphorylcholine (meth)acrylate include 2-(meth)acryloyloxyethyl phosphorylcholine.

Monomers other than the (meth)acrylic esters are not particularly limited, but include (meth)acrylic acids, ethylene and vinyl esters.

The (meth)acrylic esters may be used alone or in combination of two or more. In this specification, the (meth)acrylic acid is a generic term for acrylic acid and methacrylic acid, and the (meth)acrylate is a generic term for acrylate and methacrylate.

Among the synthetic resins, it is preferable to use a polyvinyl acetal resin. Hereinafter, a description is made of the polyvinyl acetal resin.

(Polyvinyl Acetal Resin)

The polyvinyl acetal resin is a resin synthesized by acetalizing polyvinyl alcohol with an aldehyde, which resin has an acetyl group, a hydroxyl group and an acetal group on the side chain.

The aldehydes for use in acetalization include aldehydes having a chain aliphatic group, a cyclic aliphatic group or an aromatic group having 1 to 10 carbon atoms. As the aldehydes, conventionally publicly known aldehydes can be used.

The type of the aldehyde is not particularly limited, but includes formaldehyde, acetaldehyde, propionaldehyde, butyraldehyde, pentanal, hexanal, heptanal, octanal, nonanal, decanal, acrolein, benzaldehyde, cinnamaldehyde, perylaldehyde, formylpyridine, formylimidazole, formylpyrrole, formylpiperidine, formylpiperidine, formyltriazole, formyltetrazole, formylindole, formylisoindole, formylpurine, formylpurine, formylbenzimidazole, formylbenzotriazole, formylquinoline, formylisoquinoline, formylquinoxaline, formylcinnoline, formylpteridine, formylfuran, formyloxolane, formyloxane, formylthiophene, formylthiolane, formylthiane, formyladenine, formylguanine, formylcytosine, formylthymine and formyluracil. The aldehyde may be a chain or cyclic one.

The aldehyde is preferably formaldehyde, acetaldehyde, propionaldehyde, butyraldehyde or pentanal, more preferably butyraldehyde.

The polyvinyl alcohol may be a copolymer with a vinyl compound. The vinyl compound includes ethylene, allylamine, vinylpyrrolidone, maleic anhydride, maleimide, itaconic acid, (meth)acrylic acid and (meth)acrylic ester.

The polyvinyl acetal resin preferably has on its part a Bronsted basic group or a Bronsted acidic group. This is because, when a part of the polyvinyl acetal resin is modified with a Bronsted basic group or a Bronsted acidic group, in serum-free medium culture containing no feeder cells or adhesive proteins, the initial fixation rate after stem cell seeding is improved and the stem cell culture becomes easier.

The Bronsted basic group is a generic term for a functional group that can receive a hydrogen ion $H^+$ from another substance. Examples of such a functional group include an amino group, an imino group, an amide group and an imide group.

Accordingly, as such a polyvinyl acetal resin, polyvinyl acetal resins are preferable containing in the skeleton at least one selected from the group consisting of a structural unit having an amine structure, a structural unit having an imine structure and a structural unit having an amide structure.

The Bronsted acidic group is a generic term for a substance that can deliver a hydrogen ion $H^+$ to another substance.

The Bronsted acidic group includes a carboxyl group, a sulfonic acid group, a maleic acid group, a sulfinic acid group, a sulfenic acid group, a phosphoric acid group, a phosphonic acid group, and salts thereof. Among them, a carboxyl group is preferable.

The method for modifying the polyvinyl acetal resin with the Bronsted acidic group is not particularly limited, but the target substance is obtained by copolymerization with the itaconic acid or (meth)acrylic acid, or by grafting.

In the present invention, the imine structure refers to a structure having a C=N bond. The modified polyvinyl acetal resin preferably has an imine structure on the side chain. In addition, the imine structure may be directly bonded to a carbon constituting the main chain of the modified polyvinyl acetal resin, or may be bonded via a linking group such as an alkylene group. Note that having the imine structure on the side chain includes having the imine structure on the graft chain of the modified polyvinyl acetal resin. Examples of the structural unit having an imine structure include a structural unit represented by the following formula (1).

[Chemical 1]

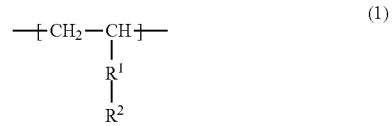

(1)

In the formula (1), $R^1$ represents a single bond or an alkylene group, and $R^2$ represents a group having an imine structure.

In the formula (1), when $R^1$ is an alkylene group, the preferred lower limit of the number of carbon atoms in the alkylene group is 1, and the preferred upper limit is 12. When the number of carbon atoms in the alkylene group exceeds 12, optimum strength may not be obtained. When $R^1$ is an alkylene group, the more preferred upper limit of the number of carbon atoms in the alkylene group is 5.

In the formula (1), when $R^1$ is an alkylene group, examples of the alkylene group includes linear alkylene groups such as a methylene group, ethylene group, trimethylene group, tetramethylene group, pentamethylene group, hexamethylene group, octamethylene group and decamethylene group, branched alkylene groups such as a methyl methylene group, methylethylene group, 1-methylpentylene group and 1,4-dimethylbutylene group, and cyclic alkylene groups such as a cyclopropylene group, cyclobutylene group and cyclohexylene group. Among them, a linear alkyl group such as a methylene group, ethylene group, trimethylene group and tetramethylene group is preferable, and a methylene group and ethylene group are more preferable.

The $R^2$ includes a functional group represented by the following formula (2).

[Chemical 2]

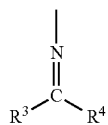

(2)

In the formula (2), $R^3$ represents a hydrogen atom or a hydrocarbon group having 1 to 18 carbon atoms, and $R^4$ represents a hydrocarbon group having 1 to 18 carbon atoms.

The hydrocarbon group includes a saturated hydrocarbon group, an unsaturated hydrocarbon group and an aromatic hydrocarbon group. The hydrocarbon group may be one composed of only a saturated hydrocarbon group, an unsaturated hydrocarbon group or an aromatic hydrocarbon group, or one in which two or more of them are used.

Examples of the saturated hydrocarbon group include methyl, ethyl, n-propyl, isopropyl, n-butyl, iso-butyl, sec-butyl, tert-butyl, pentyl, hexyl, heptyl, 2-ethylhexyl, octyl, nonyl, decyl, undecyl, dodecyl, tridecyl, tetradecyl, pentadecyl and octadecyl groups. Among them, a methyl group, ethyl group, n-propyl group and n-butyl group are preferable.

Examples of the aromatic hydrocarbon group include a phenyl group, toluyl group, xylyl group, t-butylphenyl group and benzyl group.

In the modified polyvinyl acetal resin, it is preferable that in the structural unit having an imine structure, $R^1$ be a single bond, $R^3$ be a hydrogen atom, a methyl group or an ethyl group, and $R^4$ be a methyl group or an ethyl group.

In the modified polyvinyl acetal resin, a preferable lower limit of the content of the structural unit having an imine structure is 0.1 mol %, and a preferable upper limit is 20.0 mol %. When the content of the structural unit having an imine structure is 0.1 mol % or more, the viscosity stability over time becomes better. When the content of the structural unit having an imine structure is 20.0 mol % or less, acetalization can be sufficiently advanced. The more preferred lower limit of the content of the structural unit having an imine structure is 1.0 mol %, and the more preferred upper limit is 15.0 mol %.

In the modified polyvinyl acetal resin, the ratio between the content of the structural unit having an imine structure and the degree of acetalization described below (the content of the structural unit having an imine structure/degree of acetalization) is preferably 0.001 to 0.5. Within the above range, high strength and excellent adhesiveness can be achieved at the same time, and the durability after adhesion can be improved.

The modified polyvinyl acetal resin preferably has a structural unit having an imino group (—NH) structure.

The modified polyvinyl acetal resin preferably has the imino group on the side chain. In addition, the imino group may be directly bonded to a carbon constituting the main chain of the modified polyvinyl acetal resin, or may be bonded via a linking group such as an alkylene group.

The modified polyvinyl acetal resin preferably has a structural unit having an amino group or an amide structure.

The modified polyvinyl acetal resin preferably has the amino group or the amide structure on the side chain. In addition, the amino group or the amide structure may be directly bonded to a carbon constituting the main chain of the modified polyvinyl acetal resin, or may be bonded via a linking group such as an alkylene group. Furthermore, the amino group may be a primary amine, a secondary amine, a tertiary amine or a quaternary amine. Among them, a primary amine is preferable from the viewpoint of the fixation of cells.

Note that having the amino group or amide structure on the side chain means having the amino group or the amide structure on the graft chain of the modified polyvinyl acetal resin.

In particular, the amino group is preferably —NH$_2$. In the present invention, the amide structure refers to a structure having —C(=O)—NH—. In particular, the structural unit having the amino group preferably is a structure represented by the following formula (3). In addition, the structural unit having the amide structure preferably has a structure represented by the following formula (4).

[Chemical 3]

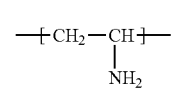

(3)

[Chemical 4]

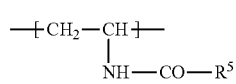

(4)

In the formula (4), $R^5$ represents a hydrogen atom or a hydrocarbon group having 1 to 10 carbon atoms. The hydrocarbon group includes an alkyl group, an alkenyl group, a cycloalkyl group and a cycloalkenyl group.

The preferred lower limit of the content of the structural unit having an amino group or an amide structure is 0.1 mol %, and the preferred upper limit is 20 mol %. When the content of the structural unit having an amino group or an amide structure is 0.1 mol % or more, additional properties can be made sufficient. When the content is 20 mol % or less, the solubility is not so excessively increased that the modified polyvinyl acetal resin powder can be easily taken out by precipitation method. The more preferred lower limit of the content is 0.5 mol %, and the more preferred upper limit is 10 mol %. The content of the structural unit having an amino group or an amide structure can be measured by NMR or the like. In addition, the preferred lower limit of the total content of the structural unit having an amino group or an amide structure and the structural unit having an imine structure is 0.1 mol %, and the preferable upper limit is 20 mol %. The more preferred lower limit of the content is 0.5 mol %, and the more preferred upper limit is 10 mol %.

In the modified polyvinyl acetal resin, the ratio between the content of the structural unit having an imine structure and that of the structural unit having an amino group or an amide structure (the structural unit having an imine structure/the structural unit having an amino group or an amide structure) is preferably 0.5/99.5 to 99.5/0.5. When the ratio is 0.5/99.5 or more, the viscosity stability over time can be sufficient, whereas when the above ratio is 99.5/0.5 or less, the crosslinking performance can be sufficiently exhibited from the viewpoint of the fixation. The more preferred lower limit of the ratio is 5/95, and the more preferred upper limit is 75/25.

The degree of acetalization of the modified polyvinyl acetal resin is not particularly limited, but the lower limit is preferably 60 mol %, and the upper limit is preferably 90 mol %. When the degree of acetalization is 60 mol % or more, the fixation of stem cells is excellent, and thus cell proliferation can be performed with high efficiency. When the degree of acetalization is 90 mol % or less, the solubility in solvent can be better. The degree of acetalization is more preferably higher than 60 mol %, still more preferably 65 mol % or more, and more preferably 85 mol % or less, still more preferably 80 mol % or less. The degree of acetal of the modified polyvinyl acetal resin can be measured by NMR or the like.

The amount of the acetyl group in the modified polyvinyl acetal resin is not particularly limited, but the lower limit is preferably 0.0001 mol % and the upper limit is preferably 5 mol %.

From the viewpoint of the cell adhesion immediately after seeding, it is preferable to contain in the skeleton of the polyvinyl acetal resin at least one functional group selected from the group consisting of a structural unit having an amine structure, a structural unit having an imine group and a structural units having an amide structure in an amount of 1 to 100.1 to 30 mol %. It is more preferable to contain mol %.

Here, a description is made of the terms used in this specification.

"Stem cell" refers to a cell having self-renew potency and differentiation potency. Among the stem cells, those that have an ability to self-renew and differentiate from one cell into all cells of endoderm, mesoderm and ectoderm are referred to as "pluripotent stem cells".

Examples of the pluripotent stem cells include induced pluripotent stem cells (hereinafter referred to as "iPS cells"), embryonic stem cells (hereinafter referred to as "ES cells"), Muse cells (multilineage differentiating stress enduring cells), embryonic cancer cells, embryonic germ cells and mGS cells (multipotent germ stem cells).

Among the stem cells, those that have an ability to self-renew, belong to any of the ectodermal, endodermal, mesodermal and germline tissues, and exhibit a limited ability to differentiate into the constituent cell types of an organ to which they belong are referred to as "tissue stem cells" and "tissue progenitor cells".

Examples of the tissue stem cells and tissue progenitor cells include neural stem cells, neural crest stem cells, retinal stem cells, corneal stem cells, keratinocyte epidermal stem cells, melanocyte stem cells, mammary gland stem cells, liver stem cells, intestinal stem cells, respiratory tract stem cells, hematopoietic stem cells, mesenchymal stem cells, cardiac stem cells, vascular endothelial progenitor cells, vascular pericytes, skeletal muscle stem cells, adipose stem cells, renal progenitor cells and sperm stem cells.

The scaffolding material for stem cell according to one aspect of the present invention allows for use as scaffolding materials for stem cells whose type is not particularly limited. Especially, the material is preferably used for culturing pluripotent stem cells, particularly iPS cells. In a serum-free medium culture containing no feeder cell or adhesive protein, the initial fixation rate of stem cells after seeding is improved, and stem cell culture can be suitably performed.

Such stem cells may include, for example, stem cells described in "Understanding It Better! Stem Cells and Regenerative Medicine (Motto Yoku Wakaru! Kansaibo to Saisei Iryo)" (Yodosha Co., Ltd., Kenji Osafune).

The lower limit of the degree of polymerization of the polyvinyl acetal resin is preferably 100, more preferably 200, still more preferably 500, even more preferably 1500. When the degree of polymerization is in the above range, the strength of the scaffolding material can be suitably maintained even when swelled in a medium to be used for cell culture, so that the cell proliferation is improved. The upper limit of the degree of polymerization is preferably 6000, more preferably 3000, still more preferably 2500. When the degree of polymerization is in the above range, the handleability is good and the scaffolding material can be suitably molded.

[Stem Cell Culture Method]

According to the scaffolding material for stem cell culture, various stem cells can be cultured. However, in consideration of the properties, among stem cells, the scaffolding material is preferably used for culturing pluripotent stem cells. This is because, although pluripotent stem cells are said to have a low fixation rate during culture after seeding in general, the scaffolding material for stem cell culture is hardly swelled with the moisture in a culture medium, and thus can maintain so suitable hydrophilicity and strength that the fixation rate of pluripotent stem cells after seeding is improved.

[Container for Stem Cell Culture]

The present invention also relates to a container for stem cell culture in which the scaffolding material for stem cell culture is used. In other words, the present invention relates to a container for stem cell culture, wherein the container for stem cell culture includes a resin film composed of the stem cell scaffolding material on at least a part of a stem cell culture region.

Figure 1B:
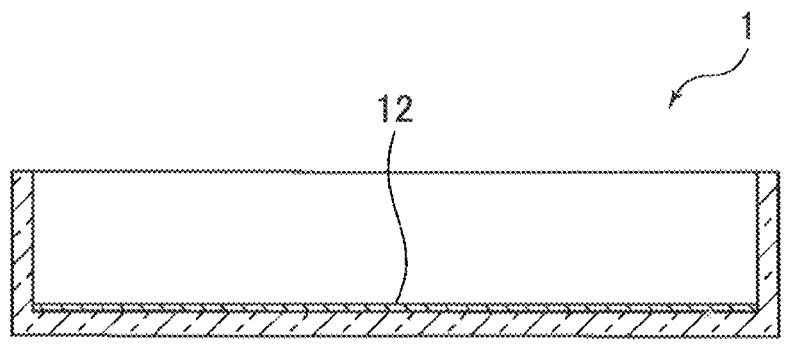
FIG. 1B is a schematic sectional side view thereof.

FIG. 1A is a schematic perspective view of the container for stem cell culture according to an embodiment, and FIG. 1B is a schematic sectional side view thereof. The container for stem cell culture is not particularly limited for shape, but examples thereof include an aspect in which a bottomed cylindrical Petri dish 1 as shown in FIG. 1A is prepared, and a resin film 12 is provided on a stem cell culture region on the bottom surface as shown in FIG. 1B.

In stem cell culture, the scaffolding material for stem cell culture can be used not only for planar culture (two-dimensional culture method) but also for culturing stem cells on a base material in a state closer to an in-vivo state, such as a porous membrane or a hydrogel (three-dimensional culture method). This is because stem cells can be efficiently proliferated by using the scaffolding material for cell culture in a bioreactor or the like.

The scaffolding material for cell culture is preferably used in a two-dimensional culture method because it has suitable hydrophilicity and strength.

The container for planar culture (two-dimensional culture method) is not particularly limited for shape and size, but includes a test plate for cell culture having one or more wells (holes) and a flask for cell culture. For example, a container for stem cell culture having six wells as shown in FIG. 2 can be used. The number of wells in the microplate is not limited, but includes, for example, 2, 4, 6, 12, 24, 48, 96 and 384.

The shape of the well is not particularly limited, but includes, for example, a perfect circle, ellipse, triangle, square, rectangle, and pentagon. The shape of the bottom surface of the well is not particularly limited, but includes a flat bottom, a round bottom and irregularities.

The material of the test plate for cell culture having one or more wells (holes) or the material of the flask for cell culture are not particularly limited, but includes a polymer resin, metal and inorganic material. The polymer resin includes polystyrene, polyethylene, polypropylene, polycarbonate, polyester, polyisoprene, cycloolefin polymer, polyimide, polyamide, polyamideimide, (meth)acrylic resin, epoxy resin and silicone. The metal includes stainless steel, copper, iron, nickel, aluminum, titanium, gold, silver and platinum. The inorganic material includes silicon oxide (glass), aluminum oxide, titanium oxide, zirconium oxide, iron oxide and silicon nitride.

In addition to the above, the scaffolding material for cell culture can be used in a suspension culture method in which stem cells are freely suspended and grown in a medium.

OTHER EMBODIMENTS

In addition to the scaffolding material for stem cell culture, the present invention provides an invention using the scaffolding material for stem cell culture as another embodiment.

For example, a carrier (medium) for stem cell culture containing the scaffolding material for stem cell culture and a polysaccharide is provided. Various polysaccharides can be used as the polysaccharide without any particular limitation. Among them, water-soluble polysaccharides are preferable.

In addition to the above, there is provided a fiber for stem cell culture including the scaffolding material for stem cell culture. In this case, it is preferable that the scaffolding material for stem cell culture be applied on the fiber. In addition, the scaffolding material for stem cell culture may be in a form impregnated or kneaded in the fiber. The fiber for stem cell culture is suitable for a three-dimensional culture method for stem cells that are difficult to adhere to a planar structure such as a flask, but easily adhere to a three-dimensional structure such as a fibril-like structure. The fiber is particularly suitable for culturing adipose stem cells among stem cells.

The scaffolding material for stem cell culture may be cross-linked. This is because crosslinking can suppress water swelling and suitably increase the strength. A crosslinking agent may be further added to the scaffolding material for stem cell culture to effect crosslinking.

The crosslinking agent is not particularly limited, but includes polyalcohol, polycarboxylic acid, hydroxycarboxylic acid, metal soap and polysaccharides.

The polyalcohol is not particularly limited, but includes ethylene glycol, propylene glycol, butanediol, pentanediol, hexanediol, heptanediol, octanediol, nonanediol, decanediol, dodecanediol, undecanediol, diethylene glycol, triethylene glycol, tetraethylene glycol, polyethylene glycol, catechol, pyrogallol, diboronic acid, methylenediboronic acid, ethylenediboronic acid, propylene diboronic acid, phenylenediboronic acid, biphenyldiboronic acid and bisphenol derivatives.

The polycarboxylic acid is not particularly limited, but includes oxalic acid, malonic acid, succinic acid, glutaric acid, adipic acid, pimelic acid, suberic acid, azelaic acid, sebacic acid, phthalic acid and poly(meth)acrylic acid.

The hydroxycarboxylic acid is not particularly limited, but includes glycolic acid, lactic acid, tartronic acid, glyceric acid, hydroxybutyric acid, malic acid, tartaric acid, cytomaric acid, citric acid, isocitric acid, leucic acid, mevalonic acid, pantoic acid, ricinoleic acid, ricineraidic acid, cerebronic acid, quinic acid, shikimic acid, hydroxybenzoic acid, salicylic acid, creosoteic acid, vanillic acid, syringic acid, pyrocatechuic acid, resorcylic acid, protocatechuic acid, gentisic acid, orsellinic acid, gallic acid, mandelic acid, benzilic acid, atrolactic acid, melilotic acid, phloretic acid, coumaric acid, umbellic acid, caffeic acid, ferulic acid, sinapinic acid and hydroxystearic acid.

The metal soap is not particularly limited, but includes salts of fatty acids such as stearic acid, lauric acid, ricinoleic acid and octylic acid with metals such as lithium, sodium, magnesium, calcium, barium, zinc and aluminum.

The polysaccharides are not particularly limited, but include pectin, guar gum, xanthan gum, tamarind gum, carrageenan, propylene glycol, carboxymethylcellulose, amylose, amylopectin, glycogen, cellulose, chitin, agarose, carrageenan, heparin, hyaluronic acid, xyloglucan and glucomannanic acid.

EXAMPLES

Hereinafter, a description is made of the present invention with reference to Examples and Comparative Examples, but the present invention is not limited to the following Examples. The content of the structural unit, for example, structural unit having an amino group (mol %), content of the structural unit having an imine structure (mol %), degree of acetalization (mol %), amount of acetyl group (mol %), amount of hydroxyl group (mol %) and the like in an obtained synthetic resin were measured by dissolving the synthetic resin in DMSO-d6 (dimethyl sulfoxide) and using $^1$H-NMR (nuclear magnetic resonance spectrum).

Example 1

(Preparation of Polyvinyl Butyral)

A reactor equipped with a stirrer was charged with 2,700 mL of ion-exchanged water, 300 g of polyvinyl alcohol having an average degree of polymerization of 300 and a degree of saponification of 99 mol %, followed by dissolution by heating with stirring to prepare a solution. Next, to the solution, 35% by mass hydrochloric acid as a catalyst was added such that the concentration of hydrochloric acid became 0.2% by mass, and after the temperature was adjusted to 15° C., 20 g of n-butyraldehyde (n-BA) was added while being stirred. Thereafter, when 130 g of n-butyraldehyde (n-BA) was added, a polyvinyl butyral resin was precipitated in the form of white particles. Fifteen minutes after the precipitation, 35% by mass hydrochloric acid was added such that the concentration of hydrochloric acid became 1.8% by mass, followed by heating to 50° C. for aging at 50° C. for 2 hours. Next, the solution was cooled and neutralized, and then the polyvinyl butyral resin was washed with water and dried.

The obtained polyvinyl butyral had an average degree of polymerization of 300, an amount of hydroxyl group of 36 mol %, an amount of acetyl group of 1 mol % and a degree of acetalization of 63 mol %.
(Preparation of Container for Cell Culture)

By dissolving 1 g of the obtained polyvinyl butyral in 19 g of butanol, a solution of polyvinyl butyral was obtained. By discharging 150 μL of the obtained solution of polyvinyl butyral onto a φ22 mm cover glass and spinning it at 2,000 rpm for 20 seconds using a spin coater, a smooth resin film was obtained. By placing the obtained resin film on a φ22 mm polystyrene dish together with the cover glass, a container for cell culture was obtained.

A test was performed on the container for cell culture provided with the resin film under the following conditions.
(Method for Cell Culture Test)

To the obtained container for cell culture, 1 mL of phosphate buffered saline was added, and the mixture was allowed to stand for 1 hour in an incubator at 37° C. After removing the phosphate buffered saline in the dish, $1.5 \times 10^4$ h-iPS cells 253G1 were seeded for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of medium, and adding 250 μL of new TeSR E8 such that the ROCK-Inhibitor (Y27632) was adjusted to be at 10 μM.
(Method for Evaluating Physical Properties of Film)
(1) Storage Elasticity A sheet was obtained having a thickness of 500 μm by stacking the obtained resin films by hot pressing. The obtained sheet was measured under tensile conditions (frequency of 10 Hz, and temperature rising rate of 5° C./min in a temperature range from −150° C. to 150° C.) caused by dynamic viscoelasticity measuring device (DVA-200, manufactured by IT Keep Measurement Control Co., Ltd.). The storage elasticity at 25° C./storage elasticity at 100° C. was calculated by determining a storage elasticity at 25° C. and a storage elasticity at 100° C. from the obtained graph of the tensile storage elasticity.
(2) Tg The peak temperature of the loss tangent was determined from the graph obtained by measurement of the storage elasticity, and was defined as a glass transition temperature Tg.
(Method for Cell Mass Culture Test)

To the obtained container for cell culture, 1 mL of phosphate buffered saline was added, and the mixture was allowed to stand for 1 hour in an incubator at 37° C. Thereafter, the phosphate buffered saline in the culture container was removed. A confluent colony of h-iPS cells 252G1 was added to a 35 mm dish, and then 1 mL of 0.5 mM ethylenediamine/phosphate buffer solution was added, followed by standing at room temperature for 2 minutes. Thereafter, the ethylenediamine/phosphate buffer solution was removed, $1.0 \times 10^5$ cell mass crushed to 50 to 200 μm by pipetting with 1 mL of TeSR E8 medium was seeded in the culture container for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of the medium and adding 250 μL of new TeSR E8.
(Evaluation Method for Culture)
(1) Drop Impact Evaluation (Evaluation of Scratch Resistance)

The presence or absence of a mark caused by drop impact when a φ 10 mm zirconia ball (YTZ-10) was dropped on the scaffolding material from a height of 1 cm was visually determined for evaluation. The judgment was made according to the following criteria.

Figure 4A:
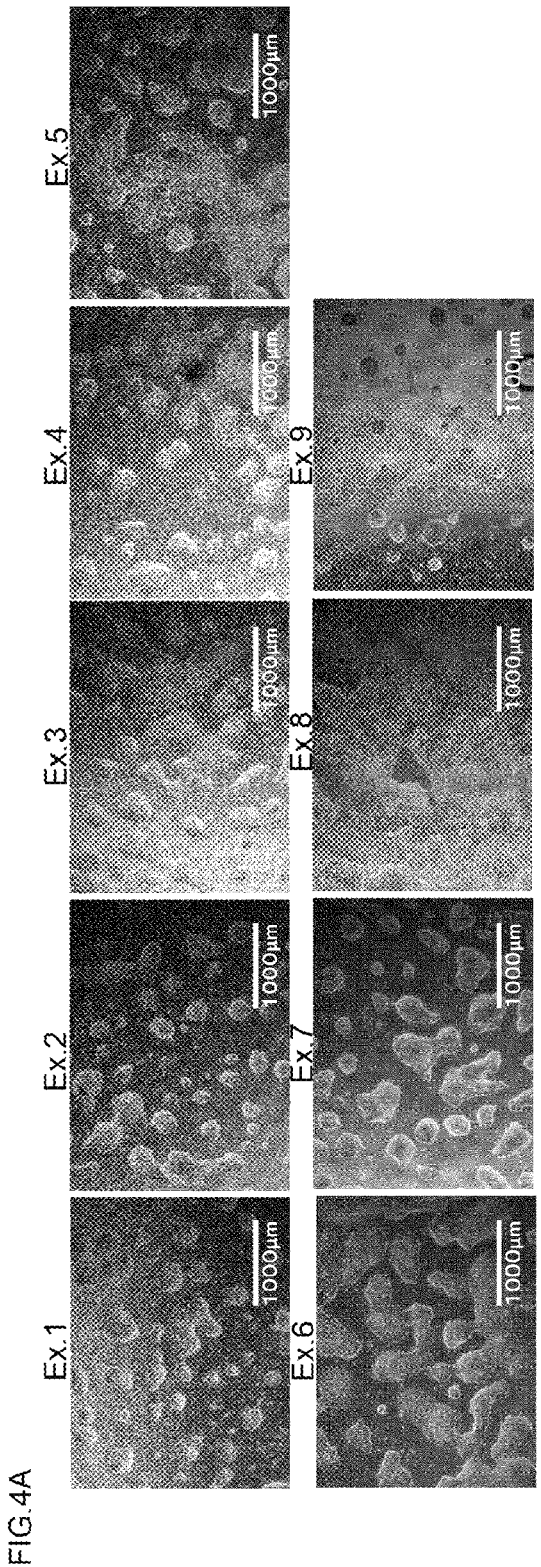
FIG. 4A and FIG. 4B are each phase contrast micrographs 5 days after cell seeding according to Examples and Comparative Examples.
Figure 4B:
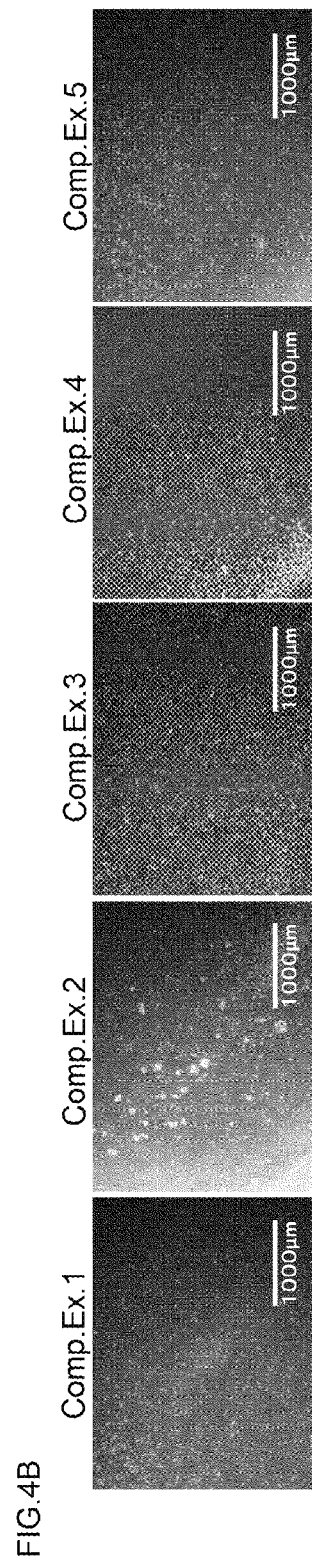

Good: No mark caused by drop impact was seen
Poor: A mark caused by drop impact was seen
(2) Cell Proliferation In the cell culture test, a cell image 5 days after the cell seeding was obtained using a phase-contrast microscope (manufactured by Olympus Corporation, IX73) at a magnification of 10×4. At that time, an image of a visual field showing the most average form of adhesion in the culture container was obtained. The cell proliferation was evaluated by comparing the obtained image with Samples 1 to 10 in FIG. 3. In FIG. 3, a higher evaluation was obtained as the colony grew due to cell proliferation. When the colony grows too much in the lateral direction (the vertical and horizontal direction in the view), it starts to pile up in the vertical direction (the direction toward the front side of the view), so that light transmittance tends to decrease. The obtained results for Examples and Comparative Examples are summarized in FIGS. 4A and 4B.

Example 2

The test was performed in the same manner as in Example 1 except that polyvinyl alcohol having an average degree of polymerization of 250 was used, and that the input amounts of n-butyraldehyde were 22 g and 148 g.

Example 3

The test was performed in the same manner as in Example 2 except that polyvinyl alcohol having an average degree of polymerization of 850 was used.

Example 4

The test was performed in the same manner as in Example 2 except that polyvinyl alcohol having an average degree of polymerization of 1,700 was used.

Example 5

The test was performed in the same manner as in Example 2 except that polyvinyl alcohol having an average degree of polymerization of 2,400 was used, and that acetaldehyde was used instead of n-butyraldehyde (n-BA).

Example 6

The test was performed in the same manner as in Example 2 except that polyvinyl alcohol having an average degree of polymerization of 850, a degree of saponification of 98 mol %, and a degree of ethylene modification of 4 mol % was used.

Example 7

The test was performed in the same manner as in Example 2 except that polyvinyl alcohol having an average degree of polymerization of 250 and a degree of saponification of 99 mol %, and containing 2 mol % structural unit having an amino group represented by the formula (3) was used.

Example 8

The test was performed in the same manner as in Example 2 except that polyvinyl alcohol having an average degree of polymerization of 1,600 and a degree of saponification of 99 mol %, and containing 2 mol % structural unit having an amino group represented by the formula (3) was used.

Example 9

In 300 parts by weight tetrahydrofuran, 48 parts by weight methyl methacrylate, 45 parts by weight butyl methacrylate and 7 parts by weight methoxymethyl acrylate were dissolved to prepare an acrylic monomer solution. In the prepared acrylic monomer solution, 2 parts by weight Irgacure184 (manufactured by BASF) was dissolved, and the resultant mixture was applied onto a PET fill. The coated product was irradiated with light having a wavelength of 365 nm at an integrated light amount of 2,000 mJ/cm$^2$ using a UV conveyor device "ECS301G1" manufactured by Eye Graphics Co., Ltd. at 25° C. to prepare an acrylic resin solution. The prepared acrylic resin solution was vacuum-dried at 80° C. for 3 hours to prepare an acrylic resin. The prepared acrylic resin was adjusted to a 3% by weight butanol solution, and the test was conducted in the same manner as in Example 1. The weight average molecular weight of the obtained resin was about 70,000.

Comparative Example 1

The test was performed in the same manner as in Example 1 using only a polystyrene dish without using the scaffolding material resin.

Comparative Example 2

The test was performed in the same manner as in Example 9 except that 100 parts by weight N-isopropylacrylamide was used for the acrylic monomer. The weight average molecular weight of the obtained resin was about 100,000.

Comparative Example 3

The test was performed in the same manner as in Example 9 except that 100 parts by weight methyl methacrylate was used for the acrylic monomer. The weight average molecular weight of the obtained resin was about 90,000.

Comparative Example 4

The test was performed in the same manner as in Example 9 except that 100 parts by weight butyl acrylate was used for the acrylic monomer. The weight average molecular weight of the obtained resin was about 120,000.

Comparative Example 5

The test was performed in the same manner as in Example 9 except that 100 parts by weight Bi-terminal Type Silaplane FM-7711 (manufactured by JNC Corporation) was used for the acrylic monomer. The weight average molecular weight of the obtained resin could not be measured for molecular weight.

The obtained results are summarized in Table 1. No differentiated cells were observed in any of the Examples and Comparative Examples.

TABLE 1

| | | | Example 1 | Example 2 | Example 3 | Example 4 | Example 5 | Example 6 | Example 7 | Example 8 |
|---|---|---|---|---|---|---|---|---|---|---|
| Synthetic resin | Polyvinyl acetal resin | Degree of acetalization (mol %) | 63 | 71 | 68 | 65 | | 64 | 77 | 77 |
| | | Amount of acetyl group (mol %) | 1 | 1 | 1 | 1 | 1 | 2 | 1 | 1 |
| | | Amount of hydroxyl group (mol %) | 36 | 28 | 31 | 34 | 33 | 30 | 20 | 20 |
| | | Content of structural unit having amino group (1) (mol %) | — | — | — | — | — | — | 2 | 2 |
| | Polystyrene resin (mol %) | | — | — | — | — | — | — | — | — |
| | Poly(meth) acrylic ester (mol %) | | — | — | — | — | — | — | — | — |
| Physical properties of film | Properties of resin | Degree of polymerization | 300 | 750 | 850 | 1700 | 2400 | 850 | 250 | 1600 |
| | Storage elasticity at 25° C. (pa) | | $2.1 \times 10^9$ | $2.2 \times 10^9$ | $2.1 \times 10^9$ | $1.5 \times 10^9$ | $2.6 \times 10^9$ | $7.1 \times 10^8$ | $2.8 \times 10^9$ | $3.7 \times 10^9$ |
| | Storage elasticity at 100° C. (pa) | | $5.2 \times 10^5$ | $2.7 \times 10^6$ | $2.8 \times 10^6$ | $3.0 \times 10^6$ | $3.4 \times 10^6$ | $3.1 \times 10^5$ | $3.1 \times 10^6$ | $3.3 \times 10^6$ |
| | Storage elasticity at 25° C./ storage elasticity at 100° C. | | $4.1 \times 10^3$ | $8.2 \times 10^2$ | $7.5 \times 10^2$ | $5.0 \times 10^2$ | $7.6 \times 10^2$ | $2.3 \times 10^3$ | $9.0 \times 10^2$ | $1.2 \times 10^3$ |
| | Tg (° C.) | | 66 | 59 | 67 | 71 | 86 | 41 | 70 | 72 |
| Evaluation for culture | Drop impact evaluation (evaluation of scratch resistance) | | Good | Good | Good | Good | Good | Good | Good | Good |
| | Cell proliferation | | 4 | 4 | 5 | 6 | 6 | 5 | 6 | 7 |

TABLE 1-continued

| | | | Example 9 | Comparative Example 1 | Comparative Example 2 | Comparative Example 3 | Comparative Example 4 | Comparative Example 5 |
|---|---|---|---|---|---|---|---|---|
| Synthetic resin | Polyvinyl acetal resin | Degree of acetalization (mol %) | — | — | — | — | — | — |
| | | Amount of acetyl group (mol %) | — | — | — | — | — | — |
| | | Amount of hydroxyl group (mol %) | — | — | — | — | — | — |
| | | Content of structural unit having amino group (1) (mol %) | — | — | — | — | — | — |
| | Polystyrene resin (mol %) | | — | 100 | — | — | — | — |
| | Poly(meth) acrylic ester (mol %) | | 100 | — | 100 | 100 | 100 | 100 |
| Properties of resin | Degree of polymerization | | 600 | 1000 | 800 | 900 | 1000 | — |
| Physical properties of film | Storage elasticity at 25° C. (pa) | | $1.2 \times 10^9$ | $2.3 \times 10^9$ | $1.4 \times 10^9$ | $3.1 \times 10^9$ | $2.7 \times 10^5$ | $4.6 \times 10^6$ |
| | Storage elasticity at 100° C. (pa) | | $1.8 \times 10^6$ | $2.1 \times 10^8$ | $5.4 \times 10^8$ | $1.2 \times 10^9$ | $2.1 \times 10^5$ | $1.6 \times 10^6$ |
| | Storage elasticity at 25° C./ storage elasticity at 100° C. | | $6.7 \times 10^2$ | $1.1 \times 10^1$ | $2.6 \times 10^0$ | $1.5 \times 10^0$ | $1.3 \times 10^0$ | $2.9 \times 10^0$ |
| | Tg (° C.) | | 56 | 100 | 334 | 105 | −55 | −102 |
| Evaluation for culture | Drop impact evaluation (evaluation of scratch resistance) | | Good | Good | Good | Good | Poor | Poor |
| | Cell proliferation | | 3 | 1 | 1 | 1 | 1 | 1 |

The invention claimed is:

1. A container for culturing a cell, comprising a container body, and a resin film provided on at least a part of a cell culture region of the container body, wherein the container is capable of culturing a cell,
the resin film comprising a scaffolding material for culturing a cell,
the scaffolding material comprising a synthetic resin, and having
a storage elasticity at 100° C. of $2.0 \times 10^5$ Pa to $1.0 \times 10^7$ Pa,
a storage elasticity at 25° C. of $1.0 \times 10^8$ Pa to $1.0 \times 10^{10}$ Pa, and
a ratio between the storage elasticity at 25° C. and the storage elasticity at 100° C. ((storage elasticity at 25° C.)/(storage elasticity at 100° C.)) of $1.0 \times 10^1$ to $1.0 \times 10^5$,
wherein the synthetic resin is a polyvinyl acetal resin.

2. The container for culturing a cell according to claim 1, wherein the container is capable of culturing a pluripotent stem cell.

3. The container for culturing a cell according to claim 1, wherein the polyvinyl acetal resin contains at least one selected from the group consisting of a structural unit having an amine structure, a structural unit having an imine structure and a structural unit having an amide structure.

4. The container for culturing a cell according to claim 1, wherein the polyvinyl acetal resin contains a structural unit having an amino group or an amide structure of 0.1 mol % to 20 mol %.

5. The container for culturing a cell according to claim 1, wherein a degree of polymerization of the polyvinyl acetal resin is 100 to 6000.

6. The container for culturing a cell according to claim 1, wherein a degree of acetalization of the polyvinyl acetal resin is 60 mol % to 90 mol %.

7. The container for culturing a cell according to claim 1, wherein the resin film has a glass transition point of 0° C. to 90° C.

8. The container for culturing a cell according to claim 3, wherein the polyvinyl acetal resin has an amino group, an amide structure or both.

9. The container for culturing a cell according to claim 8, wherein the polyvinyl acetal resin has an amino group.

10. The container for culturing a cell according to claim 8, wherein the polyvinyl acetal resin has an amino group or an amide structure on its graft chain.

11. The container for culturing a cell according to claim 1, wherein the container is a test plate having one or more wells or a flask.

12. The container for culturing a cell according to claim 1, wherein the storage elasticity at 100° C. is $3.0 \times 10^5$ Pa to $1.0 \times 10^7$ Pa.

13. The container for culturing a cell according to claim 1, wherein the storage elasticity at 100° C. is $3.2 \times 10^5$ Pa to $1.0 \times 10^7$ Pa.

* * * * *